(12) United States Patent
Robioneck et al.

(10) Patent No.: US 7,147,643 B2
(45) Date of Patent: Dec. 12, 2006

(54) IMPLANTATION SYSTEM AND AIMING DEVICE FOR THE SAME

(75) Inventors: Bernd Robioneck, Preetz (DE); George Anastopoulos, Athens (GR); Christian Lutz, Kiel (DE)

(73) Assignee: Stryker Trauma GmbH (DE)

( * ) Notice: Subject to any disclaimer, the term of this patent is extended or adjusted under 35 U.S.C. 154(b) by 387 days.

(21) Appl. No.: 10/464,245

(22) Filed: Jun. 17, 2003

(65) Prior Publication Data

US 2004/0039393 A1    Feb. 26, 2004

(30) Foreign Application Priority Data

Jun. 20, 2002    (DE)    ................. 102 27 379

(51) Int. Cl.
*A61F 5/00* (2006.01)
*A61B 17/58* (2006.01)

(52) U.S. Cl. .................. 606/86; 606/87; 606/98

(58) Field of Classification Search .......... 606/62, 606/64, 65, 67, 86, 87, 88, 96, 98
See application file for complete search history.

(56) References Cited

U.S. PATENT DOCUMENTS

| | | | |
|---|---|---|---|
| 4,697,585 A | 10/1987 | Williams | |
| 4,913,137 A * | 4/1990 | Azer et al. | 606/64 |
| 5,176,681 A | 1/1993 | Lawes et al. | |
| 5,433,720 A * | 7/1995 | Faccioli et al. | 606/87 |
| 5,454,813 A | 10/1995 | Lawes | |
| 5,643,258 A * | 7/1997 | Robioneck et al. | 606/54 |
| 5,658,287 A | 8/1997 | Hofmann et al. | |
| 5,928,235 A * | 7/1999 | Friedl | 606/64 |
| 6,039,739 A * | 3/2000 | Simon | 606/64 |
| 6,136,037 A | 10/2000 | Hässig et al. | |
| 6,514,253 B1 * | 2/2003 | Yao | 606/53 |

FOREIGN PATENT DOCUMENTS

| | | |
|---|---|---|
| EP | 0 355 411 A1 | 2/1990 |
| EP | 0 715 832 A2 | 6/1996 |

OTHER PUBLICATIONS

George Anastopoulos, MD, et al., "Closed Interlocked Nailing In Comminuted And Segmental Femoral Shaft Fractures," The Journal of Trauma, vol. 35, No. 5, Nov. 1993, pp. 772-775.

* cited by examiner

*Primary Examiner*—Pedro Philogene
(74) *Attorney, Agent, or Firm*—Lerner, David, Littenberg, Krumholz & Mentlik, LLP

(57) ABSTRACT

An implantation system for a locking nail has an aiming device, wherein the locking nail is formed for detachable attachment to the aiming device at the one end thereof. The nail has two locking holes on the other end and has an exterior feature such as a groove connecting the locking holes which groove is parallel to the axis, or indentations or elevations running in the perimeter direction in the region of the locking holes. The aiming device has a rigid aiming arm with a free end portion having three aiming bores arranged in a plane generally parallel to the axis. The outer two of the aiming bores are located at a distance from each other which corresponds to the distance of the distal locking holes of the locking nail. The system further has a connecting piece universally movable on the aiming arm. The connecting piece has an accommodation aperture for selective detachable attachment to a rod-like nail adapter which, on its part, has a coupling for detachable attachment of the locking nail.

29 Claims, 5 Drawing Sheets

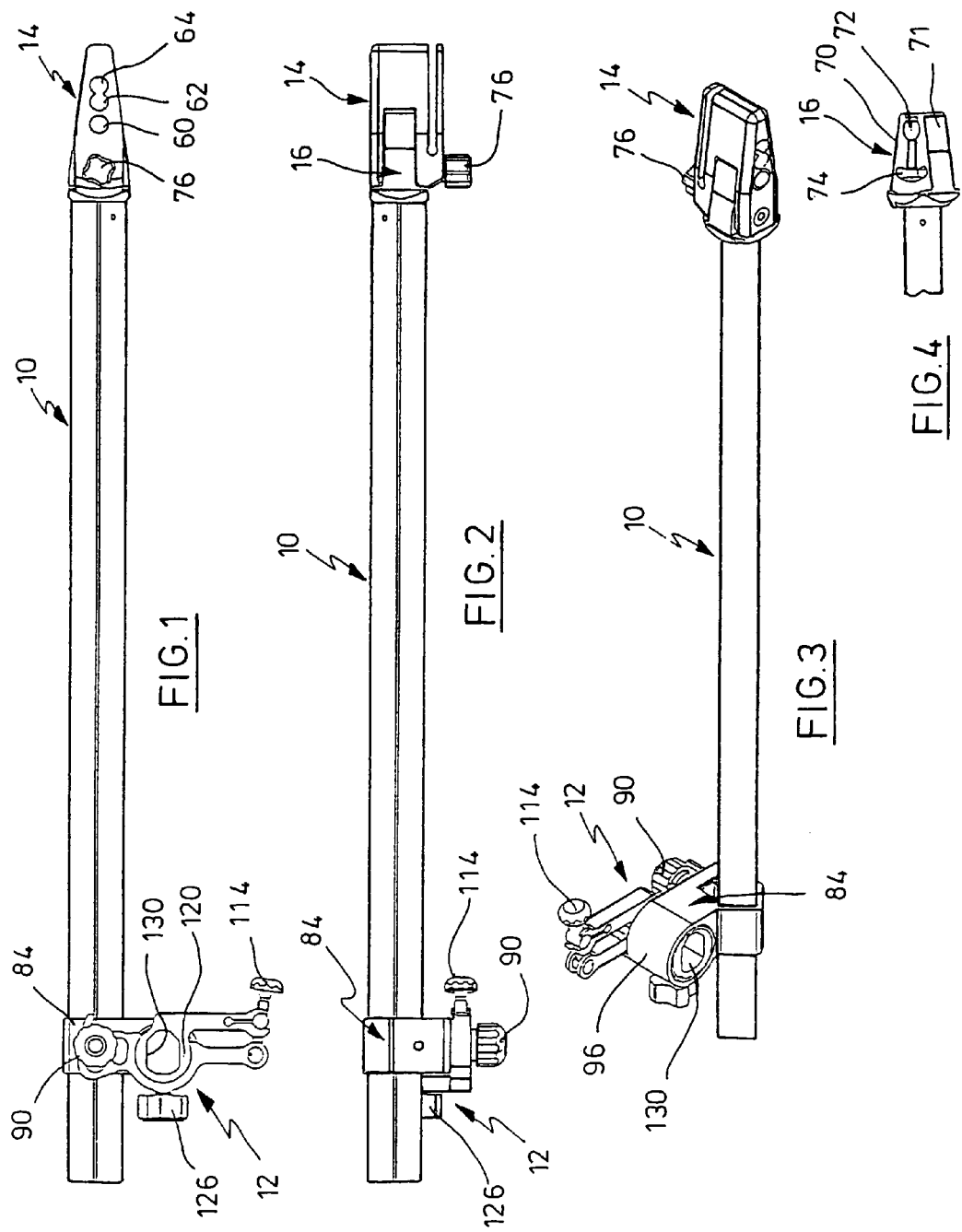

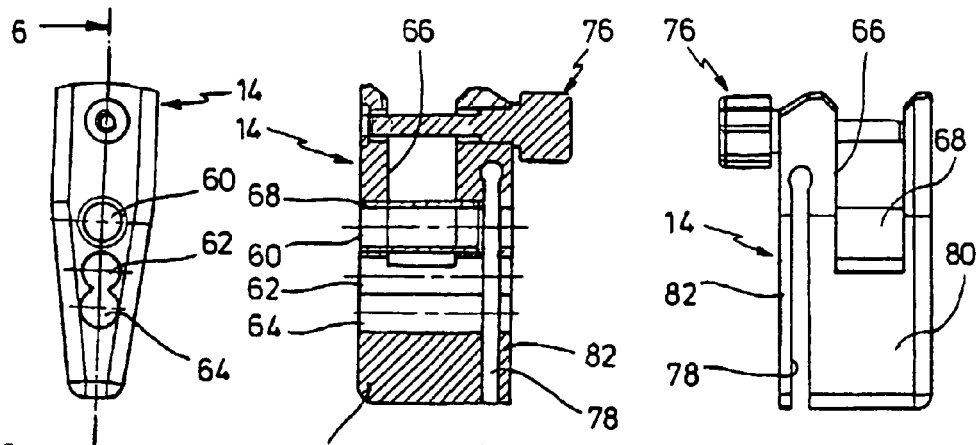
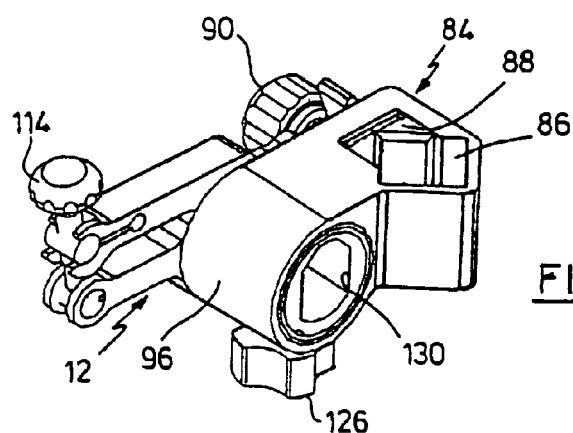
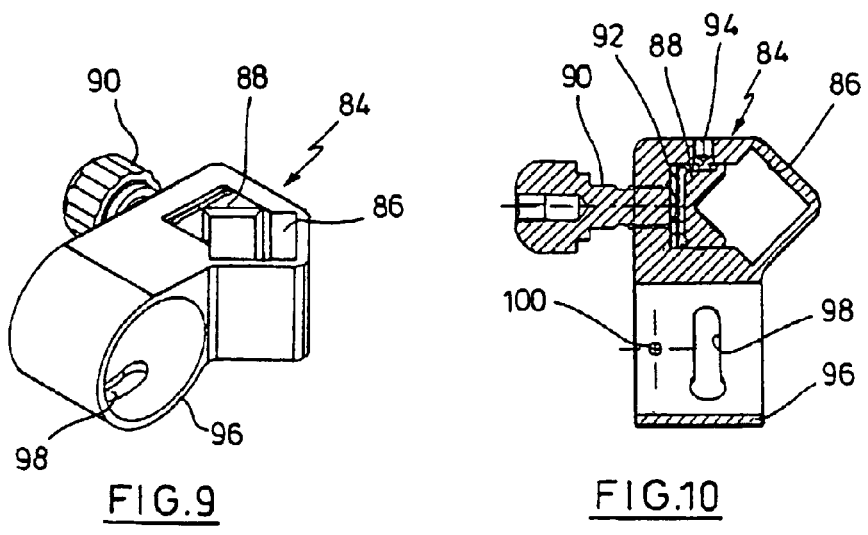

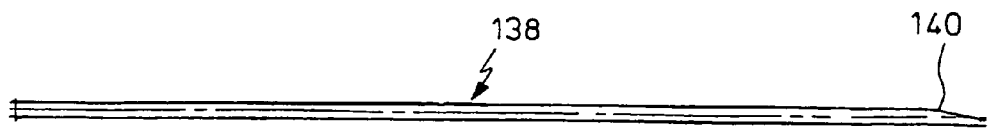
FIG.14
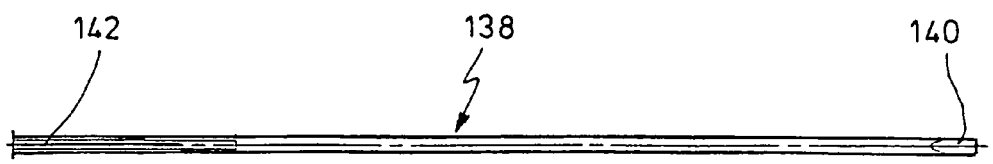
FIG.15
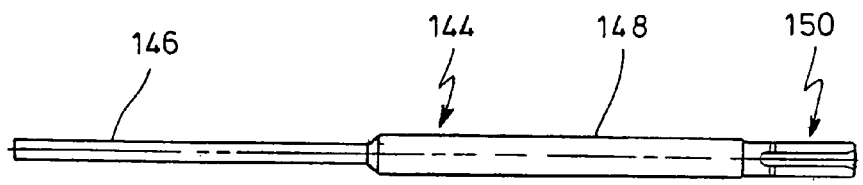
FIG.16
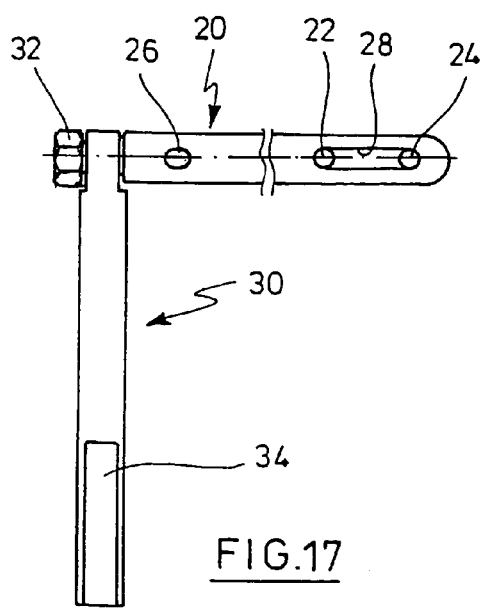
FIG.17
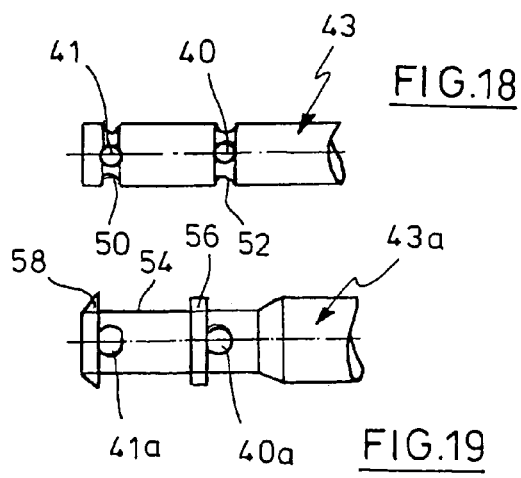
FIG.18
FIG.19

IMPLANTATION SYSTEM AND AIMING DEVICE FOR THE SAME

BACKGROUND OF THE INVENTION

The invention relates to an implantation system for locking nails used in fracture fixation.

Locking nails for the operative repairs of fractures of tubular bones are widely used. For example, application is described in "The Journal of Trauma" of 1993, Vol. 35 No. 5, p. 772 to 775. Typical for such locking nails is the arrangement of two transverse bores, i.e. cross-bores at one end (the distal end, for instance) and at least one transversal bore on the other end (the proximal end, for instance). Bone screws are guided through the transverse bores, which are screwed in at opposing sides into the cortical substance of the bone. Through this, the locking nail is secured axially and against rotation.

When using such locking nails, the position of the transverse bores or locking holes in the locking nail has to be identified, so that the cortical substance of the bone is drilled from the right place from the outside. To do this, a series of aiming or targeting devices has become known, which conveniently operate with X-rays in order to determine the position of the transverse bores with respect to the aiming device. In this case, the bone is drilled in the proper place with the aid of the aiming device and a so-called drilling or aiming sleeve, so that the bone screws can be screwed in. Known aiming devices are conveniently connected to one end (for example, the proximal end) of the nail. In this way, the correspondence of the locking holes to aiming bores in the aiming device is approximately determined. However, it has to be taken into account that by reason of the bone's curvature and possible rotation of the nail upon it being driven into the bone, the expected position of the locking holes does not coincide with the actual one.

For this reason, it has been difficult to perform an accurate identification of the position of the locking holes only by mechanical procedures.

From WO 01/60272 A1, published Aug. 23, 2001 (U.S. Ser. No. 10/203,492 filed Nov. 15, 2002, which is assigned to the Assignee of the present invention, the teachings of which are incorporated herein by reference), a locking nail is disclosed in which a groove parallel to the nail axis is formed in the nail shaft only in the distal portion in the region of the locking holes. The leading axis of the groove cuts the axis of the bore approximately perpendicularly. In the mentioned document, an aiming device is also described, the aiming arm of which is provided with two aiming bores. The aiming bores are formed in a portion of the aiming arm of the aiming device which is elastically yielding. With the aid of a thin rod-like feeler, the actual position of the nail in the bone is determined with the aid of the locking holes and the groove between them. By turning the nail and by axial displacement it can be detected when the feeler is in the region of a locking hole.

It has been found that this purely mechanical method still poses problems for the surgeon, because he cannot always determine in a sufficiently accurate manner the actual position of the nail by actuating the feeler.

SUMMARY OF THE INVENTION

The invention therefore has as one objective to provide an implantation system and an aiming device, respectively, by which the position of the locking holes can be determined in a simple manner and the bores in the bone can be seated at the proper place. This and other objects are provided by an implantation system which has at least one locking nail and an aiming or targeting device wherein the locking nail is attached to the aiming device at one end thereof. The nail has at least two locking holes on an opposite second end and has an exterior surface element, such as a groove, adjacent the locking holes. The aiming device has a rigid aiming arm with a free end aiming or guide portion having at least two and preferably at least three aiming bores arranged in a plane parallel to or in a plane including the longitudinal axis of the nail. In any case, the axes of the aiming bores can be aligned with the corresponding axes of the locking nail bores. The outer two aiming bores are spaced at a distance from each other which corresponds to the distance between the two locking holes of the locking nail. The aiming arm has a connecting piece movable on the aiming arm and being attachable thereto, wherein the connecting piece has an aperture for accommodating a detachable nail adapter which can be attached to one end, usually the exposed end, of the locking nail.

The free end aiming portion of the mounting arm is rotatably mounted around an axis perpendicular to the longitudinal axis of the aiming arm and includes a first locking element for locking the free end portion in a predetermined rotational position. The rotational axis may coincide with the axis of the interior aiming bore of the at least three bores. The aiming portion is divided in the region of the aiming bores into a narrower portion and a broader portion by a recess parallel to an axis perpendicular to the axis of the aiming bores.

The nail adapter may be rotatably mounted in the connecting piece and include a locking element to set the rotational position of the nail adapter and the connecting piece in relation to each other. An adjustor may be provided between the connecting piece and the nail adapter to adjust the relative rotational position therebetween. The aiming arm may be formed as a bar with a noncircular cross-section, which bars extends through a complimentary aperture in the connecting piece and wherein one wall of the aperture is formed by a clamping element which can be actuated by a clamping screw.

The invention also relates to a method for locating a pair of axially spaced cross-bores in the first end of a locking nail implanted in a bone canal using the apparatus of the present invention. The method includes mounting the aiming device on a second end of the nail, the aiming device having an arm portion extending generally parallel to the longitudinal axially extent of the nail and having a guide bore portion swivel mounted on a free end of the aiming arm for movement at least in a direction perpendicular to the axially extent of the arm. The guide bore portion has at least two axially spaced bores therein and preferably three axially spaced bores. The outer bores of said at least two bores and preferably three bores are spaced at a distance equal to the axial distance between the cross-bores and the first end of the locking nail. A bore in the bone adjacent one of the cross-bores is drilled by using one of the axially spaced bores on the aiming arm preferably the middle hole. After the bore is drilled, the guide bore portion is removed to allow access to the drilled hole. Alternatively, if the guide bore portion is coupled to the aiming arm, the entire aiming arm/guide bore portion can be removed. If the guide portion is modular, it, alone, may be removed. Using the hole drilled in the bone as an access port, one of the nail cross-bores is located by feel, if necessary, by manipulating the axial and rotational position of the nail. To facilitate this, the nail is either initially inserted a distance greater than its required distance or a distance less than its required distance to enable the surgeon to determine whether the cross-bore found is closer to the first or second ends of the nail. A location pin is then placed in the located nail cross-bore and the guide bore portion is remounted by aligning the corresponding bore and the guide bore portion with the location pin mounted in the cross-bore. The other nail cross-bore can then be drilled.

A connecting element may be placed between the second end of the nail and the aiming arm, which connecting element allows for universal movement of the aiming arm and, therefore, the guide bore portion at its free end, with respect to the nail so that the bores in the guide bore portion may be accurately aligned in any desired position.

The locking nail in the inventive implantation system is provided with an apparatus with the aid of which the position of the locking holes can be detected. For instance, one means consists in disposing a groove parallel to the axis between the locking holes. Another means consists in providing perimeter grooves in the region of the locking holes or alternatively suitable stops, which can be detected with the aid of a feeler.

However, one feature of the present aiming system is that the aiming arm is rigid and has an aiming or guide bore portion, in which three aiming bores are preferably provided. The axes of the aiming bores are situated in a plane which runs in the longitudinal axis of the aiming arm or parallel to it. The distance of the outer aiming bores corresponds to the distance of the locking holes. The middle aiming bore may be placed anywhere between the outer aiming bores, for example, at half the distance of their separation. The locking nail is detachably connectable to a nail adapter, for example, by a suitable threaded joint. The nail adapter is detachably connectable with a connecting piece, which on its part is detachably connectable with the rigid aiming arm. The detachable connection of the nail adapter with the aiming arm makes the use of the inventive aiming device possible for a plurality of different locking nails, without requiring a separate aiming device for each type of locking nail. Through the adjustment between the adapter at the one side and aiming arm on the other side, the nail can be adjusted in relation to the aiming arm before implantation. This takes place in a simple manner by, for example, aligning the outer aiming bores of the aiming portion of the aiming arm with the locking holes of the nail with the aid of a calibrating pin. Consecutively, the nail can be implanted, the nail adapter being allowed to remain fixed on the nail.

The locking nail is now either hammered in farther than its required end position or less far than the desired end position. Next, the aiming device is reassembled and the cortical substance of the bone on the near side is drilled via the middle of the three aiming bores. Thereafter, the aiming device is detached from the nail adapter again and a rod-like feeler is put through the bone bore. The feeler will impinge against the closed wall of the locking nail and in the most favorable case into the groove which connects the locking holes. By turning the nail the groove may be found, for example, and it can be confirmed that it is in fact engaged by the feeler. Then, the nail is drawn out or is driven in farther, until the feeler cooperates with the respective locking hole.

Next, the aiming device is mounted again, and one of the outer aiming bores is aligned with the detected locking hole. To do this, several possibilities may be contemplated. Preferably, an attachment sleeve is used, which is provided with a nearer portion with a diameter which corresponds to the diameter of the of the locking hole, and another portion, with a diameter corresponding to that of the aiming bore. The interior diameter of the attachment sleeve is dimensioned such that it can be pushed on the rod-like feeler, which is still present in the locking hole and the bone bore. Thus, a rather accurate alignment of an aiming bore with a locking hole can be achieved, by mounting the aiming arm again and pushing the one of its aiming bores onto the fixing sleeve. When this has been done, the second aiming bore in the aiming arm is also aligned with the second locking hole, and the cortical substance of the bone can be drilled above the second locking hole in the known manner, so that consecutively the seating of the locking screw can occur. When the first locking has been performed, the second locking can take place also, by drilling the cortical substance of the bone via that aiming bore, by which alignment had previously occurred, in order to seat the second locking screw.

As already mentioned, the locking nail is provided with means, such as a groove, in the region of the locking holes by which the feeling and the detection of a locking hole is facilitated. It is also theoretically conceivable, however, to get along without such means, assuming only the locking nail has not been rotated around the diameter of the locking hole upon driving in. If this is the case, the surgeon knows the rotational position of the holes best, the surgeon does not know how far the nail has to be pulled out or driven in, until the axial position of the locking hole is reached.

For calibration, in the spirit of the invention, it is preferred that the aiming portion be rotatably mounted around an axis perpendicular to the longitudinal axis of the aiming arm and be provided with first attachment means for fixing the aiming portion in a predetermined swiveling position. Preferably, the swiveling axis is situated on the axis of that aiming bore, which is nearest to the other end of the nail.

According to another embodiment of the invention, the aiming portion is provided with a slit parallel to the axis in the region of the aiming bores, which extends perpendicular to the axes of the aiming bores and subdivides the aiming portion into a narrower and a broader portion. In this way, a clamping effect is achieved upon seating in of the calibrating pin, drilling sleeve or the like, so that these parts do not unintentionally slip or fall out.

According to another embodiment of the invention, the calibration is further facilitated if the nail adapter is mounted rotabably around it longitudinal axis in the connecting piece and second attachment means is provided to fix the relative swiveling position. According to another form of the invention, an adjustor is provided between the connecting piece and the nail adapter for the adjustment of the relative swiveling position. The adjustor may contain an adjustment screw or the like for example.

The rigid aiming arm of the inventive aiming device is preferably formed as an oblong bar with noncircular cross-section, which is inserted into a complementary aperture of the connecting piece, one wall of the aperture being formed by a clamping element, which can be actuated by a clamping screw. Thus, the connecting piece can be axially adjusted continuously on the aiming arm, the angular position remaining unchanged.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

FIG. 1 shows an aiming device according to the invention in a lateral view;

FIG. 2 shows a lateral view rotated at 90° from the aiming device shown in FIG. 1;

FIG. 3 shows the aiming device according to FIGS. 1 and 2 in a perspective representation;

FIG. 4 shows the end of an aiming arm of the aiming device according to FIGS. 1 to 3;

FIG. 5 shows an end view of an aiming portion of the aiming device according to FIGS. 1 to 3;

FIG. 6 shows a section through the end view of FIG. 5, along the line 6—6;

FIG. 7 shows the end view of the aiming portion according to FIG. 5 rotated at 90°;

FIG. 8 shows in perspective the connecting and the calibrating piece of the aiming device according to FIGS. 1 to 3;

FIG. 9 shows the connecting piece of the structure according to FIG. 8;

FIG. 10 shows a section through the connecting piece according to FIG. 9;

FIG. 14 shows the side view of a feeler;

FIG. 15 shows a side view, of the feeler according to FIG. 14 rotated 90°;

FIG. 16 shows the lateral view of a fixing sleeve;

FIG. 17 shows the lateral view of a locking nail, as well as a nail adapter attached thereto;

FIG. 18 shows a second embodiment for the end of a nail;

FIG. 19 shows yet another embodiment for the end of the locking nail; and

DETAILED DESCRIPTION

Figure 11:
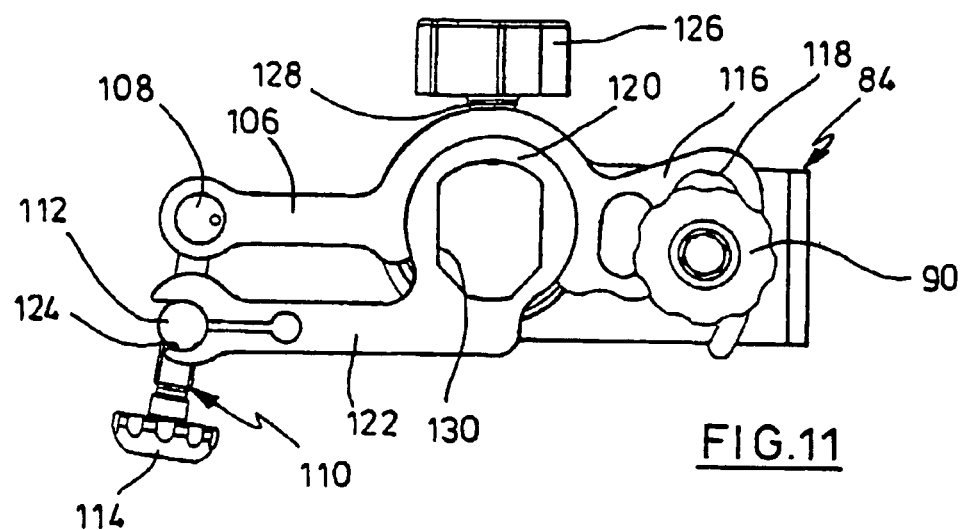
FIG. 11 shows a side view of the connecting and calibrating piece according to FIG. 8.

Referring to FIGS. 1 to 3, there is shown an aiming arm 10, which, in the preferred embodiment, has a square cross-section. On the left end of aiming arm 10 in FIG. 1, a calibrating and connecting piece 12 is seated, and on the right end an aiming portion 14 is shown. Aiming portion 14 is rotatably mounted on a suitable bearing portion 16 on the right end of aiming arm 10.

Locking nails for which the aiming device according to FIGS. 1 to 3 is applicable are represented in FIGS. 17 to 19. In FIG. 17 a locking nail 20 is shown, for instance a femoral nail. Nail 20 is provided with two axially spaced apart locking holes or cross-bores 22, 24 on the distal end, and a locking hole or cross-bore 26 on the proximal end. A groove 28 extends parallel to the nail axis and in the preferred embodiment has a U- or V-shaped cross-section between the locking holes 22, 24. The outer diameter of locking nail 20 is connected to an oblong nail adapter 30, preferably with the aid of a screw 32, which is screwable into the proximal end of nail 20. On the other end, nail adapter 30 is provided with flat portions 34 facing each other.

In FIG. 18, a second embodiment of the end of a locking nail 43 is shown, with locking holes 40, 41 and diametric grooves 50, 52 in the region of the locking holes 40, 41. In FIG. 19 locking holes 40a, 41a are shown, which are formed in a distal end portion reduced in diameter of the locking nail 43a. On the left side of the locking holes 40a, 41a, respectively, radial collars 56, 58 are formed, the collar 58 being chamfered towards the left end. The function of the nail forms shown can also be used in the process set forth below. Grooves 50, 52 and flanges 56, 58 can be used to detect the location of the cross-bores.

As may especially be seen from the FIGS. 5 to 7, the preferred aiming portion 14 is provided with at least two and preferably three aiming bores 60, 62, 64, the axes of which are situated in a plane which goes through the longitudinal axis of aiming arm 10 or runs parallel to it. The axial separation of the outer aiming bores 60, 64 corresponds to the distance of the locking holes 22, 24 or 40, 41 or 40a, 41a, respectively. As follows from FIGS. 6 and 7, the aiming portion 14 is provided with a first relatively broad recess 66, with a width marginally larger than the width of bearing portion 16. As follows from FIG. 4, bearing portion 16 is formed fork-like with arms 70, 71, which have an extension 72 adjacent and between the ends of the arms 70, 71, which have an extension 72 near to the ends of the arms 70, 71 and an arcuate slit 74 running transversely on the end of the arms 70, 71. From FIGS. 6 and 7, it follows that the recess 66 is traversed by the shank of a fixing screw 76, the diameter of the shank being somewhat smaller than the width of arcuate slit 74 of bearing portion 16. On the inner end, the recess 66 is traversed by a bearing sleeve 68. It is possible that recess 66 could be made solid such as by using a pivot pin leaving only the two outer bores 60, 64. When bearing portion 16 is introduced into the slit, the shank of the fixing screw 76 is placed in the arcuate slit 74 and the sleeve 68 in the extension 72. Thus, the aiming portion 14 is rotatably mounted around the axis of the sleeve 68 in the bearing portion 16. The relative swiveling position is fixed by the fixing screw 76.

The aiming portion 14 is also subdivided by a relatively narrower slit 78, which is introduced from the direction of the free end of the aiming portion 14, into a relatively broad portion 80 which is provided with recess 66, and a relatively narrower portion 82. The latter is flexible in a limited degree in relation to the former and has bores, which are aligned with the aiming bores 60, 62 and 64.

In FIGS. 8 to 10, a preferred connecting piece 84 is represented, with the aid of which the nail adapter can be maintained movable and detachable on the aiming arm 10, for instance, according to FIG. 17. In the preferred embodiment, connecting piece 84 is provided with a square aperture 86 of a cross-section corresponding to the cross-section of the aiming arm 10. A clamping portion 88 is movably mounted in the connecting piece 84 and forms a corner portion of the aperture 86. The portion 88 is actuated by a clamping screw 90, which acts upon a relatively thin portion 92 of the portion 88, which is separated from the remaining portion 88 by a slit similar in form to portion 82 and slit 78 of portion 14, in order to obtain a spring-like effect. A pin 94, which seats in a groove of portion 88, limits the adjustment of portion 88.

Connecting piece 84 additionally is provided with a bearing sleeve 96, the axis of which runs perpendicular to the axis of the accommodation aperture 86. A slot 98 is formed in the bearing sleeve 96 which slit has an extension in the diametral direction. Further, a pin 100 is press fit in bearing sleeve 96, which pin protrudes somewhat from the interior of the bearing sleeve 96.

Figure 12:
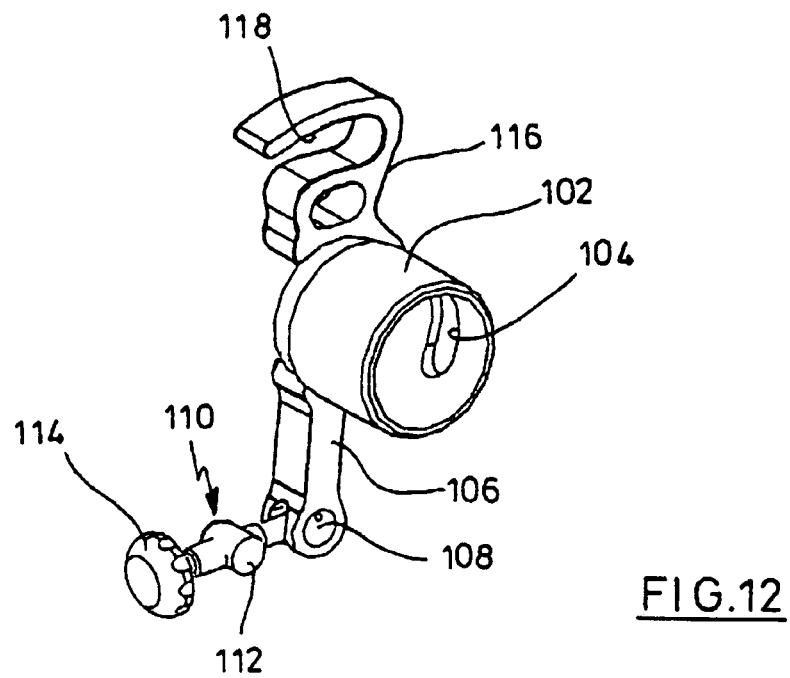
FIG. 12 shows a detail of the arrangement according to FIG. 11.

In FIG. 11, the other side of the calibrating and connecting piece as shown in FIG. 8 is represented in a lateral view. In FIG. 12, a preferred sleeve portion 102 is shown which is provided with a slot 104 partially extending into the diametral direction. The sleeve portion 102 is dimensioned such that it can be inserted into the bearing sleeve 96, the slots 98 and 104 at least partially allowed to come into congruence. On one end of the sleeve portion is attached an arm 106 on which is pivotally mounted an adjustment screw 110 at point 108. Screw 110 is provided with a cylindrical locking bolt 112 which is provided with an internal thread. The operation of the screw 110 takes place via a rotary knob 114, which, upon rotation, acts to move bolt 112. An arm 116 opposite the arm 106 is formed on the sleeve portion 102 at the same cylindrical end surface, which arm has a bent flange 118 open towards the one side. In the sleeve portion 102 there is situated an additional sleeve portion 120, on which an arm 122 is formed. On the free end of the arm 122 a circular recess 124 is formed, which accommodates the cylindrical locking bolt 112. Thus, upon a rotation of the knob 114 a relative swiveling between the arms 106 and 122 takes place. With a knob 126 a fixing screw 128 is actuated, which engages into a thread bore (not shown) of the sleeve portion 120. The shank of the screw 128 extends through the slots 98 and 104 of bearing sleeve 96 and sleeve portion 102. The sleeve portion 102 has a noncircular aperture 130 for the accommodation of the end portion of the nail adapter 30. With the aid of fixing screw 128 the axial position of the nail adapter in the aperture 130 can be fixed. By swiveling the arm 122 in relation to the connecting piece 84, the nail adapter can be turned around its axis and, by doing so, can perform a swiveling of the nail 20. The relative swiveling position of the sleeve portion 102 and the arms 106 and 116, respectively, with respect to the connecting piece 84 is effected by the fixing screw 90, the shank of which extends through the bent flange 118.

Figure 13:
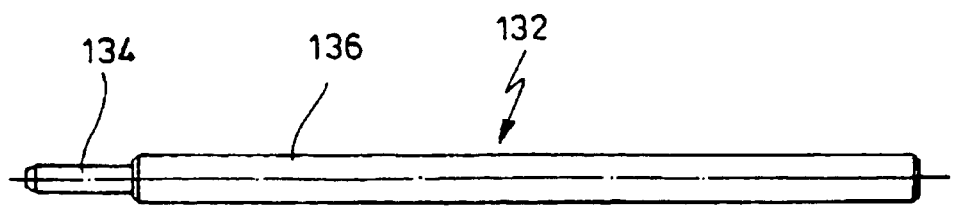
FIG. 13 shows the side view of a calibrating pin.

In FIG. 13, a calibrating pin 132 is shown, with a left portion 134 of smaller diameter and a relatively long portion 136 of larger diameter. The diameter of the portion 134 corresponds to the diameter of locking holes 26, 24 and 40, 41 and 40a, 41a, respectively. The diameter of portion 136 corresponds to the diameter of aiming bores 60, 62 and 64, respectively.

In FIGS. 14 and 15 a feeler or location 138 is shown, which has a circular cross-section of a relatively small diameter over its length, which is significantly smaller than the diameter of the locking holes. On one end the feeler 138 is chamfered, as shown at 140, for the formation of a kind of cutting edge. On the other end, the feeler pin or location pin 138 has opposing flats 142, for the purpose of clamping into a grip or handle portion (not shown).

In FIG. 16 a fixing sleeve 144 is represented with a portion 146, the exterior diameter of which corresponds to the diameter of the locking holes 22, 24 and 41, 40, 41a, 40a, respectively. A portion 148 has a larger diameter, which corresponds to the diameter of the aiming bores 60 to 64. On the right end, the aiming sleeve 144 is provided with a clamping portion 150 for the purposes of a detachable connection with a handle. The aiming sleeve 144 has a continuous axial bore with a diameter roughly matching that of pin 138 such that the feeler pin 138 can be pushed through it.

Figure 20:
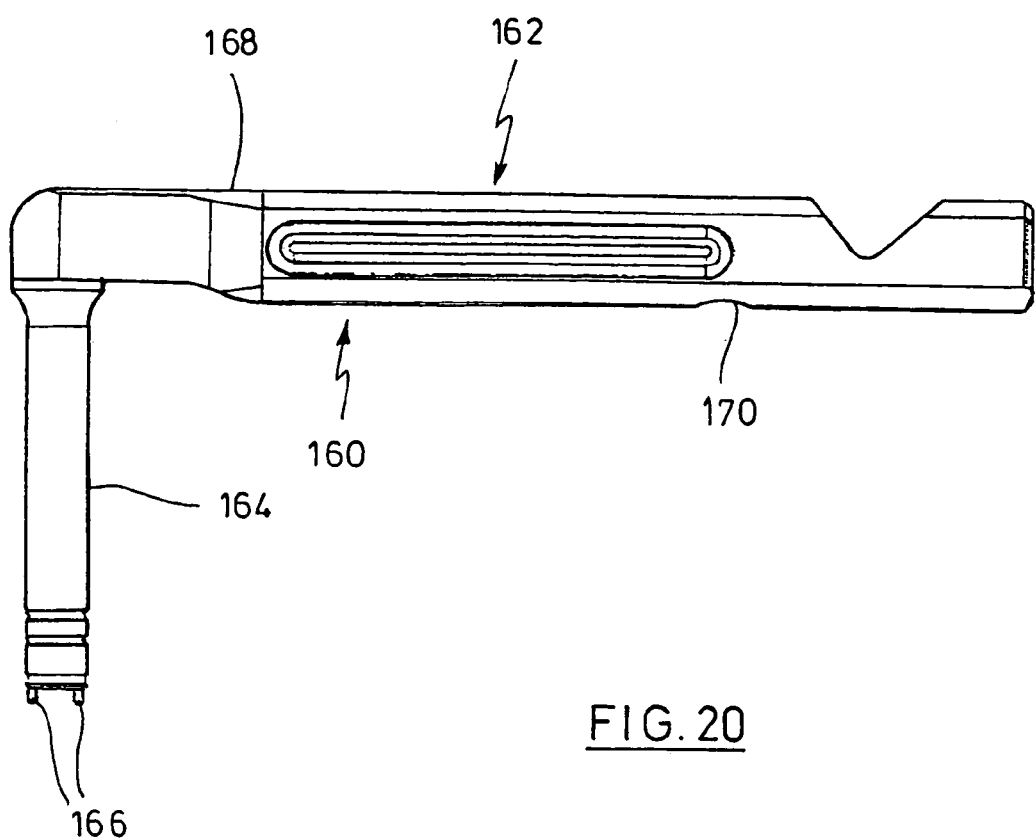
FIG. 20 shows the lateral view of a nail adapter for the system according to the preceding figures.

The nail adapter 160 shown in FIG. 20 has a shaft 162, the cross-section of which is complementary to the cross-section of the aperture 130 in the connecting piece 84 (see for example FIG. 8). On the left end of the shaft 162, an adapter portion 164 is attached to shaft 162 with the aid of a screw connection (not shown). Adapter portion 164 has two protrusions 166 on the free end, which engage in corresponding recesses of the nail (not shown), in order to predetermine its angular position. The nail is then fixed on the adapter 160 with the aid of a screw connection which extends through the hollow portion 164 in a known manner.

At 168 and 170, respectively, bores through the shaft 162 are indicated, which can also be used as aiming or alignment bores.

The described implantation system is employed as follows. Firstly, a calibration is performed. The nail to be implanted, for example, nail 20 in FIG. 17, is connected with the nail adapter 30. Nail adapter 30 is inserted into aperture 130 of the connecting piece and is fixed with the aid of clamping screw 126. By axially adjusting connecting piece 84 on aiming arm 10 and, as the case may be, by swiveling the nail by actuating the adjustment screw 114, locking holes 22, 24 are aligned with aiming bores 60, 64. At first, an alignment with respect to the aiming bore 60 takes place by inserting a calibrating pin according to FIG. 13. Optionally, a drill bit guiding sleeve and a drill may be used for this purpose. In that, the portion 134 of calibrating pin 132 arrives in the locking hole 22. Subsequently, aiming portion 14 is swiveled so far until the aiming bore 64 is also aligned with the locking hole 24, which can be detected with the aid of the calibration pin. Thereafter, a fixing of the aiming portion 14 in the actual swiveling position with the aid of the fixing screw 76 takes place. The position of the nail had been previously adjusted by the clamping screw 126, fixing screw 90 and adjustment screw 114. Subsequently, the nail adapter 30 is removed by disengaging clamping screw 126, and locking nail 20 is driven into the bone in the conventional manner, for example, from the proximal position into the femur channel. The nail adapter 30 remains attached on locking nail 20. Locking nail 20 is driven in for a certain distance somewhat farther than the desired end position. This oversize corresponds to a distance which is smaller than the separation of locking holes 22, 24. After the nail has been driven in, a fixing of aiming arm 10 on nail adapter 30 takes place in the already described way. Now, a hole is drilled into the cortical substance on the near side of the bone through middle aiming bore 72 with the aid of a suitable drilling sleeve and, as the case may be, a tissue protection sleeve. In doing this, care must be taken to avoid the drill coming into contact with the nail 20. After this hole is drilled, the aiming device is subsequently removed from the nail adapter, and an attempt is made to feel the groove 28 with the aid of the feeler 138, which is pushed through the bone bore. If this fails, the groove 28 can be detected by feel by slightly turning the nail 20 in the bone channel. As soon as this occurs, the nail 20 is somewhat pulled out, until the feeler 22 detects the locking hole 24 by feel. When this is done, the fixing sleeve 144 is placed over the feeler 138. In this, the portion 146 arrives in the locking hole 24 through the bone bore. The aiming device is subsequently mounted anew with the fixing sleeve 144 seated in this way, the aiming bore 64 being aligned to the fixing sleeve 144. When the fixing of the aiming device has taken place, the inner aiming bore 60 is automatically aligned to the inner locking hole 22. Now the bone can be drilled on opposing sides of the locking hole 22 with the aid of the conventional methods and a locking screw can be inserted, in order to fix the nail in the bone. When this has taken place, the cortical substance of the bone can be drilled also on the other side by also removing the fixing sleeve 144 and with the aid of the conventional methods, in order to incorporate a locking screw also into this region.

As soon as the distal locking is ended, a locking in the region of the proximal locking hole 26 can also take place in known manner.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantation system comprising a locking nail and an aiming device, wherein the locking nail has at a first end a means for selective attachment to the aiming device, the nail has two locking holes on an opposite second end and has an exterior surface feature adjacent the locking holes, and wherein the aiming device has a rigid aiming arm with a free end aiming portion having at least three aiming bores generally aligned with a longitudinal axis of the nail, two outer aiming bores of said at least three aiming bores are spaced at a distance from each other which corresponds to a distance between the locking holes at the second end of the locking nail, said aiming device further has a connecting piece movable on the aiming arm and being fixable thereon, wherein the connecting piece has an aperture for accommodation of a detachable nail adapter which includes said means for selective attachment of the locking nail wherein the free end aiming portion of the aiming arm is rotatably mounted around an axis perpendicular to the longitudinal axis of the aiming arm and comprises first locking means for the locking of the free end portion in a rotational position.

2. The system according to claim 1 wherein the rotational axis coincides with the axis of an interior aiming bore of said at least three bores.

3. The system according to claim 2 wherein the aiming portion is divided in the region of the aiming bores into a narrower portion and a broader portion by a recess parallel to an axis perpendicular to the axis of the aiming bores.

4. The system according to claim 1 wherein the nail adapter is rotatably mounted in the connecting piece and a second locking means is provided to fix the rotational position of nail adapter and connecting piece in relation to each other.

5. The system according to claim 1 wherein an adjusting means is provided between the connecting piece and the nail adapter for the adjustment of the relative rotational position.

6. The system according to claim 1 wherein the aiming arm is formed as a bar with noncircular cross-section, extending through a complementary aiming arm aperture of the connecting piece, wherein one wall of the aperture is formed by a clamping element which can be actuated by a clamping screw.

7. The system according to claim 6 wherein the nail adapter has a noncircular shaft portion which is accommodated within a complementary adapter accommodation aperture of a first sleeve portion in a movable and fixable manner, the first sleeve portion being accommodated rotatably in a bearing sleeve of the connecting piece, the axis of which runs approximately perpendicular to the axis of the aiming arm aperture of the connecting piece and a third fixing means is provided which fixes the relative angular position of the first sleeve portion and the bearing sleeve.

8. The system according to claim 7 wherein the connecting piece has a first arm connected with the first sleeve portion, a second sleeve portion is disposed between bearing sleeve and the first sleeve portion, said second sleeve is provided with a second arm, the second sleeve portion has a third arm, which is fixable in different rotational positions on the connecting piece, and an adjustment screw is disposed between the first and the second arm for the adjustment of the distance of the arms with respect to each other.

9. The system according to claim 8 wherein the third arm has an arcuate slot through which a fixing screw extends, which engages a threaded bore of the connecting part.

10. The system according to claim 9 wherein the fixing screw simultaneously fixes at the aiming arm on the connecting piece in an axial and a rotational position.

11. The system according to claim 8 wherein a second fixing screw extends through the bearing sleeve and the second sleeve portion and is seated in a threaded bore of the first sleeve portion in order to fix the nail adapter.

12. The system according to claim 1 wherein a calibrating pin is provided with an end portion, a diameter of which corresponds to a diameter of the locking holes, whereas the remaining shaft has a diameter which corresponds to a diameter of the aiming bores.

13. The system according to claim 1 wherein a locating pin is provided, having an outside diameter which is smaller than a diameter of the locking holes and which has a point or a cutting edge on one end thereof.

14. The system according to claim 13 wherein an oblong fixing sleeve is provided, the inside diameter of which corresponds to the outside diameter of the locating pin, which has a first portion with an outside diameter corresponding to a diameter of the locking holes, and which has a second portion with an outside diameter corresponding to a diameter of the aiming bores.

15. The system according to claim 1 wherein the connecting piece is provided with a clamping element which engages the aiming arm and the clamping element has a resilient portion, against which a fixing screw bears.

16. The system according to claim 15, wherein the resilient portion is formed by a slit.

17. The system according to claim 1 wherein a rotational axis of the aiming portion and the longitudinal axis of the aiming arm are situated in a plane parallel to longitudinal axis of the nail.

18. An aiming device for a locking nail having a first end which is detachably connectable with the aiming device and has at a second end two spaced apart locking holes comprising:
a rigid aiming arm extending generally parallel to a longitudinal axis of the locking nail and having aiming bores, said aiming bores being alignable with the locking holes of the locking nail;
a nail adapter for detachably coupling the aiming arm to said nail, said adapter is selectively movably received in a first aperture of a connecting piece positioned between the nail adapter and the aiming arm;
the aiming arm being movable in a longitudinal direction within a second aperture of the connecting piece and may be fixed therein longitudinally with respect to said nail; and
the aiming arm having an end portion with at least two aiming bores, the distance between the two aiming bores corresponding to a distance between the locking holes wherein the end portion of the aiming arm is rotatably mounted around an axis perpendicular to said longitudinal axis and includes a locking element to lock the end portion in a rotational position.

19. The aiming device as set forth in claim 18 wherein the end portion of the aiming arm can swivel in a direction generally perpendicular to the longitudinal direction.

20. The aiming device as set forth in claim 18 wherein the aiming arm end portion has three bores with the outer holes spaced the distance between the locking holes.

21. The aiming device as set forth in claim 18 wherein the arm of the nail adapter is rotatably received in the first aperture.

22. The aiming device as set forth in claim 21 further including a screw mounted on said connecting piece for locking the aiming arm in a desired position with respect to the longitudinal nail axis.

23. A method for locating a pair of axially spaced cross-bores in a first end of a locking nail implanted in a bone canal comprising:

mounting an aiming device on a second end of said nail, said aiming device having an arm portion extending generally parallel to the longitudinal axial extent of said nail and having a guide bore portion forming an end of said arm portion swivel mounted on a free end thereof for movement in a direction perpendicular to said axial extent of said arm, said guide bore portion having at least two axially spaced bores therein, the outer bore of said at least two bores being spaced a distance equal to an axial distance between said cross-bores;

rotating and locking the guide bore portion in position;

drilling a bore in the bone through one of said axially spaced bores on the arm guide bore portion;

removing the guide bore portion;

locating by feel through said bore in the bone the location a first of said nail cross-bores, if necessary, by manipulating the axial and rotational position of said nail;

placing a location pin in said located cross-bore; and remounting the guide bore portion by aligning one of the axially spaced bores therein with the location pin.

24. The method as set forth in claim 23 further comprising drilling the bone adjacent the second nail cross-bore through said other bore in said guide bore portion.

25. The method as set forth in claim 23 further comprising inserting said nail in the bone a distance greater than a desired distance.

26. The method as set forth in claim 25 further comprising aligning the bore of said guide bore portion closest to said nail first end with said location pin.

27. The method as set forth in claim 20 further comprising inserting said nail in the bone a distance less than a desire distance.

28. The method as set forth in claim 27 further comprising aligning the bore of said guide bore portion closest to said nail second end with said location pin.

29. An aiming device for a locking nail having a first end which is detachably connectable with the aiming device and has at a second end two spaced apart locking holes comprising:

a rigid aiming arm extending generally parallel to a longitudinal axis of the locking nail and having aiming bores, said aiming bores being alignable with the locking holes of the locking nail;

a nail adapter for detachably coupling the aiming arm to said nail, said adapter is selectively movably received in a first aperture of a connecting piece positioned between the nail adapter and the aiming arm;

the aiming arm being movable in a longitudinal direction within a second aperture of the connecting piece and may be fixed therein longitudinally with respect to said nail; and the aiming arm having an end portion with at least two aiming bores, the distance between the two aiming bores corresponding to a distance between the locking holes wherein the nail adapter is rotatably mounted in the connecting piece and a second locking means is provided to fix the rotational position of nail adapter and connecting piece in relation to each other.

\* \* \* \* \*

UNITED STATES PATENT AND TRADEMARK OFFICE
CERTIFICATE OF CORRECTION

| | |
|---|---|
| PATENT NO. | : 7,147,643 B2 |
| APPLICATION NO. | : 10/464245 |
| DATED | : December 12, 2006 |
| INVENTOR(S) | : Bernd Robioneck, George Anastopoulos and Christian Lutz |

It is certified that error appears in the above-identified patent and that said Letters Patent is hereby corrected as shown below:

Column 2, Line 38 "extends" should be replaced by --extend--.

Column 5, Line 30 "," following the word "view" should be deleted.

Column 10, Line 39 insert --the-- after the word "to".

Column 11, Line 28 insert --of--after the word "location".

Column 12, Line 6 "desire" should be replaced by --desired--.

Signed and Sealed this

Twenty-eighth Day of August, 2007

JON W. DUDAS
*Director of the United States Patent and Trademark Office*